United States Patent [19]

Platus

[11] Patent Number: 5,709,471
[45] Date of Patent: Jan. 20, 1998

[54] METHOD FOR THERMALLY TESTING WITH A LASER THE EDGE OF A SAPPHIRE WINDOW

[75] Inventor: Daniel H. Platus, Rancho Palos Verdes, Calif.

[73] Assignee: The Aerospace Corporation, El Segundo, Calif.

[21] Appl. No.: 608,805

[22] Filed: Feb. 29, 1996

[51] Int. Cl.$^6$ .............................. G01N 3/60; G01N 25/00
[52] U.S. Cl. ............................................................ 374/57
[58] Field of Search ................................ 374/57, 5, 15, 374/4

[56] References Cited

U.S. PATENT DOCUMENTS

| | | | |
|---|---|---|---|
| 4,043,177 | 8/1977 | Swift | 374/57 |
| 4,468,136 | 8/1984 | Murphy et al. | 374/57 |
| 4,632,561 | 12/1986 | Rosencwaig et al. | 374/57 |
| 4,710,030 | 12/1987 | Tauc et al. | 374/57 |
| 4,752,140 | 6/1988 | Cielo et al. | 374/57 |
| 5,131,758 | 7/1992 | Heyman et al. | 374/57 |

FOREIGN PATENT DOCUMENTS

| | | | |
|---|---|---|---|
| 0158334 | 8/1985 | Japan | 374/57 |
| 81/03704 | 12/1981 | WIPO | 374/5 |

OTHER PUBLICATIONS

"High Performance Sapphire Windows" by S. C. Bates, Conference Paper 3rd National Technology Transfer Conference and Exposition, vol. 2, pp. 460–469, Feb. 1993 (only abstract considered).

"Arcjet Exploratory Test of ARC Optical Window Design for the AFE Vehicle" by E. E. Whiting,. et al., AAIA Technical Library, Apr. 1991 (only abstract considered).

"Thermal Shock Testing of Optical Ceramics", by D. Lewis, III, SPIE vol. 297, Emerging Optical Materials, Aug. 25, 1981, Conference Proceedings; International Society for Optical Engineering, pp. 120–124, 1982.

*Primary Examiner*—Diego F. F. Gutierrez
*Attorney, Agent, or Firm*—Derrick Michael Reid

[57] ABSTRACT

A sapphire window is laser edge tested using a $CO_2$ laser spot illuminating along a path following the periphery of the optical surface of the window so as to diffuse heat towards the edges which may crack and fail if defective with subsurface defects which are likely to cause stress fractures when stressed.

3 Claims, 1 Drawing Sheet

METHOD FOR THERMALLY TESTING WITH A LASER THE EDGE OF A SAPPHIRE WINDOW

STATEMENT OF GOVERNMENT INTEREST

The invention was made with Government support under Contract No. F$\phi$4701-93-C-0094 by the Department of the Air Force. The Government has certain rights in the invention.

The invention described herein may be manufactured and used by and for the government of the United States for governmental purpose without payment of royalty therefor.

STATEMENT OF RELATED APPLICATION

The present patent application is related to applicant's copending application Ser. No. 08/611,113, filed: Mar. 3, 1996, entitled Sapphire Window Laser Edge Annealing.

SPECIFICATION

FIELD OF THE INVENTION

The present invention relates to the field of laser spot acceptance testing. More particularly, the present invention relates to laser spot testing of sapphire windows which may be used in high speed missiles, missile interceptors, rockets, seekers and or atmospheric re-entry vehicles.

BACKGROUND OF THE INVENTION

Various high velocity missiles, missile interceptors, rockets, seekers and atmospheric re-entry vehicles may require the use of a window through which optical signals, such as laser beams or infrared radiation, may be used to acquire land based facilities or airborne targets. Specifically, high performance interceptor missiles employ infrared seekers to track incoming targets and guide the interceptor to these targets. An essential component of the interceptor is the seeker window which must be transparent to the infrared radiation and be able to structurally withstand aerodynamic pressure loading and intense aerodynamic heating. The preferred seeker window material is a single crystal sapphire because sapphire optical properties are well suited for infrared transmission and sapphire thermal mechanical properties make the sapphire resistant to thermal stress fracture relative to other available window materials.

These sapphire windows are subjected to excessive stress during flight. These flight stresses may cause cracking, breakage or failure of the window. The sapphire window is potentially a performance limiting component of an high velocity interceptor missile. Typically, the edge of the window is secured to a window frame through edge clamping using molding. In some specific applications, the window may be made of sapphire and the window edge may be beveled and adapted in shape to be mounted within a vehicle window frame and securely clamped by the window molding. Computer analyses and thermal stress fracture testing of sapphire windows indicate that failure under simulated flight loading occurs at the window edge because the highest thermal stresses that cause fracture occur at the window edge and because the window is weakest at the edges from machining damage during fabrication which produces microscopic flaws in a small layer at the window edge surface. Machining damages the top layer which has much lower strength than the undisturbed bulk single crystal sapphire. The window optical surfaces of the window surface area is also subject to machining and polishing damage but the nature of the flight induced thermal stresses and polishing of these flat surfaces are such that thermal fracture is much less likely to occur at these surfaces than at the window edges. There exists a need to manufacture and test the windows which are resistance to stresses at the edges of the windows.

For application as a high velocity flight window, the sapphire window is polished for improved optical transmission through the window. Chemical etch polishing, abrasive polishing, and flame polishing may be used to polish ceramic materials. Abrasive polishing is preferred because of the precision and simplicity of the abrasive polishes without the use of dangerous chemicals used in chemical etch polishing nor the use of imprecise flame polishing or flame annealing. Flame polishing has been shown to increase the strength of small sapphire specimens by up to an order of magnitude, but flame polishing degrades polished optical surfaces. Defect testing must not degrade the polished optical surfaces.

Sapphire is known to be a relatively brittle ceramic. Brittle ceramic materials generally fail due to tension stresses. Sapphire high velocity flight windows may be subject to tension stresses at the edges. There exists a need to improve the stress resistance testing of edges of high velocity ceramic windows. Sapphire windows will include micro defects which may fracture and fail under stress. There is a need for a simple and inexpensive acceptance test to ascertain the fabrication damage and resulting thermal structural integrity of sapphire seeker windows.

The window fabrication process involves growing a single crystal sapphire boule, followed by successive sawing, grinding and polishing operations, which are believed to cause residual stresses and sub surface damage in the form of microscopic flaws. X-ray diffraction methods can examine the window for the extent of defects in the window during and after fabrication. This method of testing is limited to the x-ray penetration depth and in the ability to adequately predict residual stresses and fabrication damage. The true test of the stress resistance of the windows is exposure to the thermal loading experienced during the flight environment. The flight environment may be simulated through the use of high enthalpy wind tunnel facilities, arc tunnels or burner facilities to subject the finished window to the expected flight thermal loading. During this simulation, the window is flood loaded, that is, it is heated over the entire window which disadvantageously requires a large and costly facility. These and other disadvantages are solved or reduced using the present invention.

SUMMARY OF THE INVENTION

An object of this invention is to improved acceptance stress resistance testing of ceramic materials.

Another object of this invention is to improve the edge stress resistance testing of sapphire windows without degrading the optical surface of the windows.

Still another object of the present invention is to provide a method for improving the edge testing of sapphire windows for thermal stress resistance without degrading the optical properties of the optical surface.

The present invention covers edge testing of optical ceramic materials. The edge testing tests the tensile strength of the window at the edge. The edge testing can be accomplished without serious degradation of the polish of any optical surfaces of the optical ceramic which is in the form of a polished window. Fabrication damage includes flaws created during machining and polishing. It has been discovered that high tensile stresses, combined with fabrication damage, will cause fractures of high velocity sapphire windows along machined beveled edges of the windows. The fractures along the edges is the most common failure mechanism of the sapphire window. The invention broadly covers edge testing of optical ceramics. In the preferred form of the invention, a sapphire window is tested using a laser. The sapphire window may be annealed in an oven as a general low temperature anneal in combination with laser edge annealing. This edge annealing improves the edge tensile strength without degrading the optical properties of the polished surface. The sapphire window may then be polished to optical specification. After annealing and polishing of the sapphire window, a laser beam spot illuminates areas of the optical surface near the edge of the window. The window is heated near the edge to simulate flight edge thermal stresses produced during operational heat loading. Defective windows will crack and fail under laser heating as edge failure is the most common type of failure. The present laser edge testing is used to remove defective parts from production parts. These and other advantages will become more apparent from the following detailed description of the preferred embodiment.

DETAILED DESCRIPTION OF THE PREFERRED EMBODIMENT

Figure 1:
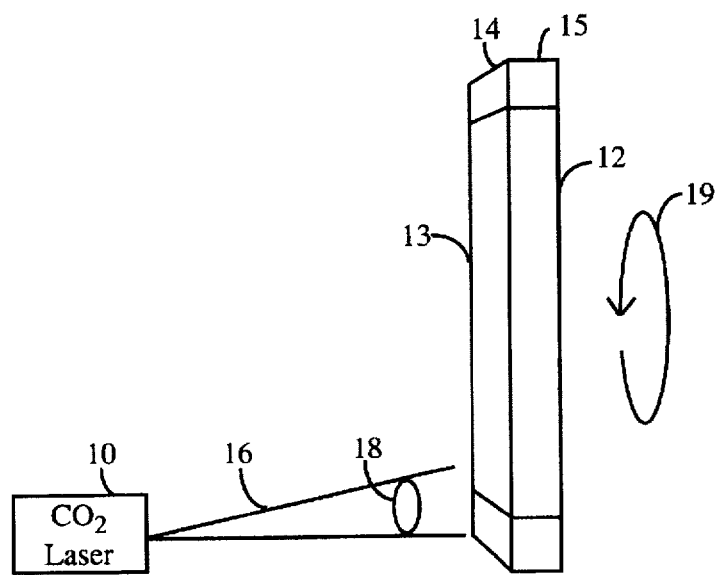
FIG. 1 is diagram showing laser edge testing of an optical ceramic window.
Figure 2:
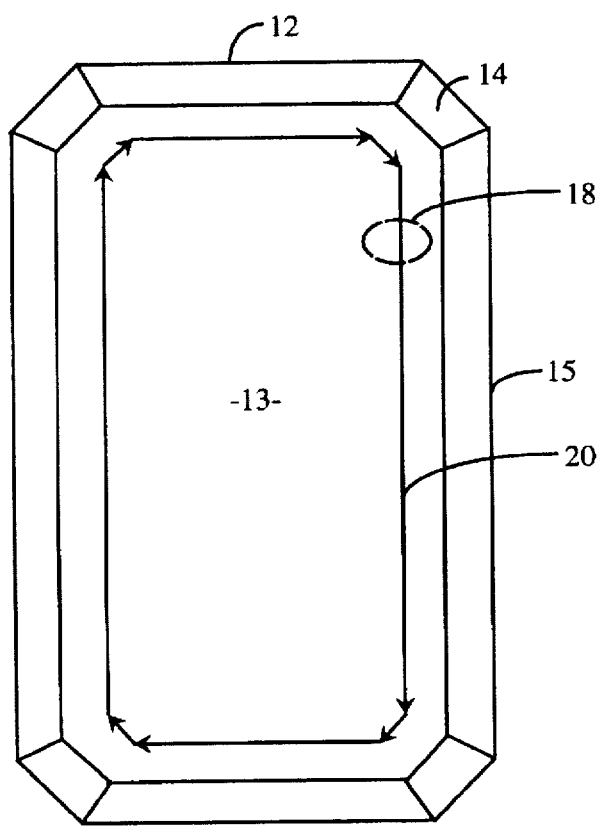
FIG. 2 is diagram showing the path of a laser spot along the edge of the optical ceramic window.

An embodiment of the present invention is described with reference to the figures using reference designations as shown in FIGS. 1 and 2. Referring to FIGS. 1 and 2, an optical means 10, which is preferably a carbon dioxide ($CO_2$) laser, illuminates an optical ceramic 12. The optical ceramic 12 is preferably a high performance seeker sapphire window. The optical ceramic 12 has an optical surface 13 defined by an edge 15, which may comprise a beveled surface 14. The ceramic 12 may be edge strength limited, in that, during use under stress, failure, if any, is likely to occur at the edge 15. The beveled surface 14 is machined into a shaped adapted for purposes of mounting the optical ceramic 12. The optical ceramic may be mounted into a window frame, not shown. The window 12 is subject to stresses during use.

The laser 10 illuminates the polished surface 13 along the periphery of the surface 13 near the edge 15 to inject a thermal gradient in the sapphire window edge to simulate flight thermal stresses. Subsurface damage of the window edge is susceptible to high edge thermal stresses. Defective windows may fracture at the edge 15 under thermal stress testing. The edge illumination increases the temperature of the window near the edge 15 to transfer thermal stresses into the edge 15 of the ceramic optical window 12. The $CO_2$ laser is suitable for performing the window edge testing because the absorption of $CO_2$ wavelength laser radiation in sapphire is relatively high causing a very thin layer of the surface exposed to the laser to heat up. Other similar lasers and other corresponding optical ceramics can be used and treated in a similar fashion. Depending on the laser power and the exposure time, a thin sub surface damage layer will be subjected to thermal stresses very similar to, but exceeding those, expected during flight. The testing temperature of the sapphire must be below the sapphire melt temperature. Heat is dissipated away from the spot toward the edge 15. Machining defects in the sapphire may become evident by cracking and failure at the edge when subjected to the stresses, thereby indicating a defective window. This manner of testing is proof testing or acceptance testing to screen out defective windows from those acceptable for flight. Alternatively, the laser power and/or exposure time could be adjusted to cause failure at the thermal stress limits of the windows to statistically determine thermal fracture limits.

The laser 10 projects a laser beam 16 having a defined spot size 18. Lasers 10 are well known to be controlled to predetermined power levels, direction and duration. Those skilled in the art of optics can readily design control means to control the laser 10 to illuminate the periphery of the surface 13 juxtapose the edge 15 of the optical ceramic 12 along the path 20. The spot illumination 18 substantially illuminates the periphery of the surface 13 near edge 15 to inject thermal gradients towards the edge 15, similar to those experienced during use. During use, the edge is thermally shadowed and insulated by the window frame and remains cooler, thereby creating temperature gradients and thermal stresses at the edge. The laser insubstantially heats the center of the optical surface 13 thereby selectively causing the edge 15 to be tested while the remaining bulk portion of the ceramic 12, and particularly the center of optical surface 13, does not substantially heat up to the flight loading temperature. The present invention replicates the maximum design-limiting thermal stresses, which occur in the window edge. Ideally, one would want to replicate flight thermal stresses over the entire window. But this would require a large, costly facility. The present invention replicates only the edge temperature gradients to produce the critical design-limiting thermal stresses.

Alternatively, the laser 10 could also be directed towards the edge to more selectively heat the edge. However, during flight, the optical surface is heated and the edge is shielded by the window frame, creating a temperature gradient towards the edge. Heating the optical surface 13 more closely simulates the flight environment than heating only the edge. But, laser edge heat testing could still detect the presence of edge damage without illuminating the optical surface. By focusing the laser beam to a small spot on the window edge, the region in the vicinity of the spot will be subjected to concentrated thermal stresses. The magnitudes of the stresses can be calculated using finite element analysis, and controlled to specified values by adjusting the laser and exposure parameters. Windows having excessive edge defects will crack under a prescribed thermal loading and can be rejected. Laser testing is controllable and can be performed with sufficient consistency to establish repeatable edge temperature gradients and design-limiting thermal stresses.

The optical means 10 in the form of a $CO_2$ laser requires power in the laser spot of typically 50 W/cm2 to 300 W/cm2 applied for one to several seconds to test an optical ceramic 12 in the form of a sapphire seeker window of approximate dimensions 10 cm wide×20 cm long×0.5 cm thick. For a typical spot size of 2 cm×2 cm, this requires a total power in the laser beam of 200 W to 1200 W. Assuming 50% losses in laser power from optics and other sources, this requires a total laser power in the range of 400 W to 2400 W. The laser spot is located typically adjacent to, but not including, the window edge by means of an aperture, e.g., the center of a 2 cm×2 cm spot is located 1 cm from the window edge. By comparison, the optical means 12 totally illuminated with the same power density requires a heat source of 10,000 W to 60,000 W, with a total power in the heating device of 20,000 W to 120,000 W, assuming the same efficiency as the laser. For a laser as the optical means 10, the laser can be located at any practical distance from the optical ceramic, e.g., 10 m to 100 m or more, with suitable optics to steer the beam and control beam divergence. The aperture that controls the spot size and location is typically located close to the optical ceramic, e.g., mm to cm, depending on the optics used to steer and focus the beam.

Alternatively, by using a focused laser beam to selectively heat a small region of the window edge, in order to detect the presence of edge damage, the total power required to generate substantial thermal stress is quite small. For a window thickness of 3 mm to 10 mm, for example, a laser spot on the order of 1 $mm^2$ to 5 $mm^2$ with a heating intensity of 1 $kW/cm^2$ to 2 $kW/cm^2$ is sufficient to fracture sapphire in one to a few seconds of exposure. The total power in the laser beam is only 10 W to 100 W.

The present invention uses an optical illumination means to spot test optical ceramics along the edges of the ceramic for improved acceptance testing of the optical ceramic. In the preferred form of the invention, the laser is a $CO_2$ laser and the optical ceramic is a beveled sapphire window. Other improved, enhanced, alternative or modified illumination sources and optical ceramic materials may used as well. However, those enhancements, improvements and modifications may nonetheless fall within the spirit and scope of the following claims.

What is claimed is:

1. A method of testing an optical ceramic having an edge and a polished optical surface with an optical surface periphery, the optical ceramic experiences loading stresses when in use, the method comprising the steps of, generating an illumination beam to be absorbed by the optical ceramic, and illuminating the optical surface periphery of the optical surface with said beam to simulate the loading stresses by creating a temperature gradient extending towards the edge to produce thermal stresses in the edge, the thermal stresses cause microcracks in the edge to fracture when the optical ceramic is defective, and the thermal stresses do not damage the polished optical surface when the optical ceramic is not defective.

2. The method of claim 1 wherein said illumination beam is a CO2 laser beam, and said optical ceramic is a sapphire window.

3. The method of claim 1 wherein said edge is a beveled edge having a beveled surface.

* * * * *